United States Patent [19]

Taheri

[11] Patent Number: 5,617,878
[45] Date of Patent: Apr. 8, 1997

[54] STENT AND METHOD FOR TREATMENT OF AORTIC OCCLUSIVE DISEASE

[76] Inventor: Syde A. Taheri, 268 Dan-Troy, Williamsville, N.Y. 14221

[21] Appl. No.: 656,671

[22] Filed: May 31, 1996

[51] Int. Cl.⁶ .................................................. A61B 19/00
[52] U.S. Cl. ................................. 128/898; 606/198; 623/1
[58] Field of Search ................................. 128/898; 623/1, 623/11, 12; 606/1, 159, 191–200; 604/96–104

[56] References Cited

U.S. PATENT DOCUMENTS

| | | |
|---|---|---|
| 4,577,631 | 3/1986 | Kreamer .................................... 623/1 |
| 4,816,028 | 3/1989 | Kapadia et al. ........................... 623/1 |
| 5,464,449 | 11/1995 | Ryan et al. ................................ 623/1 |

Primary Examiner—Glenn Dawson
Attorney, Agent, or Firm—Hodgson, Russ, Andrews, Woods & Goodyear

[57] ABSTRACT

A method of treating arterial disease at the intersection of two arteries using both a graft and stent. The graft is placed at the intersection of two arteries by the use of a balloon catheter. A device is used to make an opening in the graft at a point corresponding to the intersection of the two arteries. A stent is inserted into the graft and through the graft opening; the stent having an attachment mechanism to attach one end of the stent to the opening in the graft whereby the flow of blood at the intersection of the arteries is ensured.

8 Claims, 11 Drawing Sheets

STENT AND METHOD FOR TREATMENT OF AORTIC OCCLUSIVE DISEASE

BACKGROUND OF THE INVENTION

The present invention relates generally to the field of the treatment of aortic occlusive disease and in particular, to an improved stent and method for treating aortic occlusive disease in or around the intersection of the aorta and attendant arteries such as the renal arteries.

According to the prior art, aortic disease is often treated by surgical techniques involving the use of stents and grafts. For example, it is well known in the art to interpose within the stenotic portion of an artery a stent, whether made of stainless steel or other materials, capable of being balloon-expandable for strengthening the walls of a stenotic or occluded artery. Similarly, it is also well known in the prior art to use a graft to repair highly damaged portions of, for example, the aorta or other arteries thereby ensuring blood flow and reducing the risk of an aneurysm or rupture. The grafts, hollow tubes comprised of material such as dacron, are normally inserted within the walls of a damaged artery and can be sewn into position or expanded through the use of a stented balloon catheter.

A more severe problem occurs when it is necessary to use a graft at or around the intersection of a major artery (e.g., the aorta) with intersecting arteries (e.g., the renal arteries, carotid or brachiocephalic artery). While the graft is clearly required to strengthened and ensure the flow of blood through, for example, the aorta, the use of a graft effectively seals or blocks off the blood flow to the kidneys or cerebral circulation. Accordingly, it is often times impossible or impractical to use a graft to treat aortic disease at or around the intersection of the aorta and other arteries. Instead, a surgeon must attempt to repair the weakened walls of such artery using other surgical techniques having high failure rates and limited success.

The present invention solves the problem in the prior art by providing a graft and improved stent for use therewith and a method for treating aortic [occlusive] disease through the use of grafts at or around an intersection point.

SUMMARY OF THE INVENTION

The present invention comprises a method and improved stent for use in the surgical treatment of aortic [occlusive] disease and in particular, to a method and improved stent for treating aortic occlusive disease at or around the intersection of various major arteries, e.g., the aorta and renal arteries, or brachiocephalic artery.

The improved stent comprises a strengthened mesh body portion having, at one end, a raised collar further including a series of protruding tines around the diameter thereof. The stent and collar are adapted to be inserted through a manufactured opening in a typical dacron or other graft by having the opening of the wall of the graft engage the collar and tines as the stent body portion extends therethrough. The stent is interposed through a graft at or around the point of intersection of a secondary artery (e.g., the point where the renal arteries and aorta intersect) thereby ensuring blood flow through the renal arteries into the aorta while ensuring the graft does not block such blood flow.

The method of the present invention includes interposition of a graft at or around the intersection of major arteries and thereafter, use of intravenous ultrasound or angiogram to visualize and measure the point on the graft where the arterial intersection occurs. A laser or cautery device is then interposed within the graft and is used to create an opening in the graft wall at the point of the intersection. The improved stent of the present invention is then, through the use of a double lumen balloon catheter interposed within the graft and through the created opening of the intersecting artery. A special collar having tines at one end of the stent is adapted to be secured tightly to the stent and to form a junction of the two arteries adapted to carry blood flow through the graft into the organ at issue. The balloon catheter is further adapted to expand the stent walls to ensure an appropriate positioning of the stent against the inner walls of the artery, while the other lumen of the catheter will supply continuous oxygenated blood into the organ while the procedure is undertaken.

The present invention also comprises an embodiment including a frusto-conical shaped stent approximating the diminishing diameter of some specific arteries, e.g., the renal arteries, to ensure an even better fit at the intersection and through the artery toward the kidneys.

Accordingly, one object of the present invention is to provide an improved stent and method for use in the treatment of aortic occlusive disease.

Still another object of the invention is to provide a method for using a well-known graft to repair an artery at or around a point of arterial intersection.

Yet another object of the invention is to provide an improved stent having particular characteristics and dimensions readily adaptable for use with the renal arteries or other arteries having varying diameters and to ensure the graft is secured to the arterial wall.

These and other objects of the invention will be apparent to one of ordinary skill in the art from the specification, the drawing figures and the following claims.

DESCRIPTION OF THE DRAWING FIGURES

DESCRIPTION OF THE PREFERRED EMBODIMENT OF THE INVENTION

Figure 1:
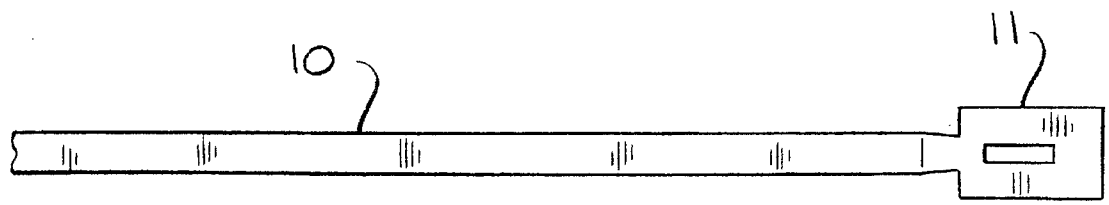
FIG. 1 is a view of a typical and well-known laser cautery device.

The present invention comprises a method and an improved stent for use in the treatment of aortic disease and in particular, employing a graft to treat occlusive aortic disease as well as another aneurysm at and around the intersection of the aorta and other major arteries, such as the renal arteries to the kidneys or brachiocephalic artery and carotid artery to the brain.

The drawing figures illustrate the basic steps comprising the method, as well as illustrate the features of the improved stent.

FIG. 1 is a side elevation of a well-known laser cautery device, 10 having at one end, a cutting appendage 11. The laser cautery device 10 is adapted to be interposed within the walls of an artery and can be used to cut away tissue or, pursuant to the present method, create an opening in the wall of an arterial graft.

Figure 2:
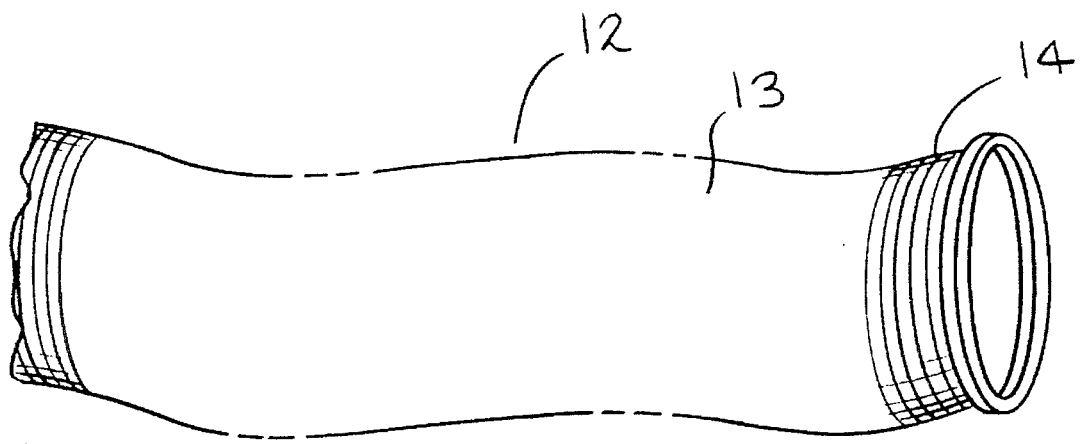
FIG. 2 is a view of a typical and well-known vascular graft.

FIG. 2 is a side elevation of a well-known arterial graft 12 used in the treatment of occlusive disease. Graft 12 comprises a cylindrical body portion 13 made of, for example, dacron and end portion 14 comprising a flexible collar and re-enforcing means. Graft 12 is inserted and positioned through various techniques (e.g., balloon catheter) into an area of a diseased artery to reinforce the walls thereof and to prevent collapse or hemorrhaging.

Figure 3:
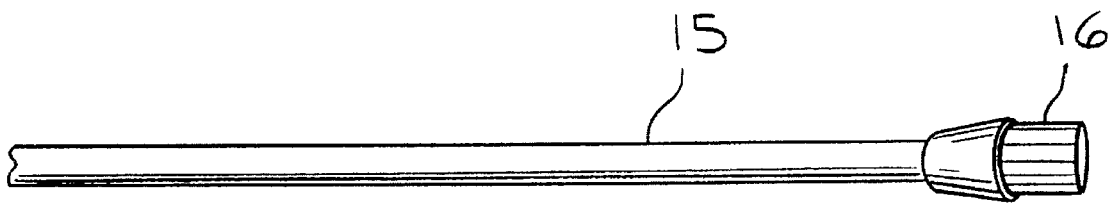
FIG. 3 is a view of a typical and well-known intravenous ultrasound device.

FIG. 3 is a side elevation of a well-known intravenous ultrasound device 15 having at its one end, a sound emitting and visualizing head portion 16. The intravenous ultrasound device (IVUS) 15 is adapted to be inserted through an artery and to transmit signals to an appropriate receptor in the operatory so the operating surgeon may visualize through sound or other video images the extent and nature of the occlusive disease and also, the exact position where intersection of, for example, the aorta and renal arteries, occurs.

Figure 4:
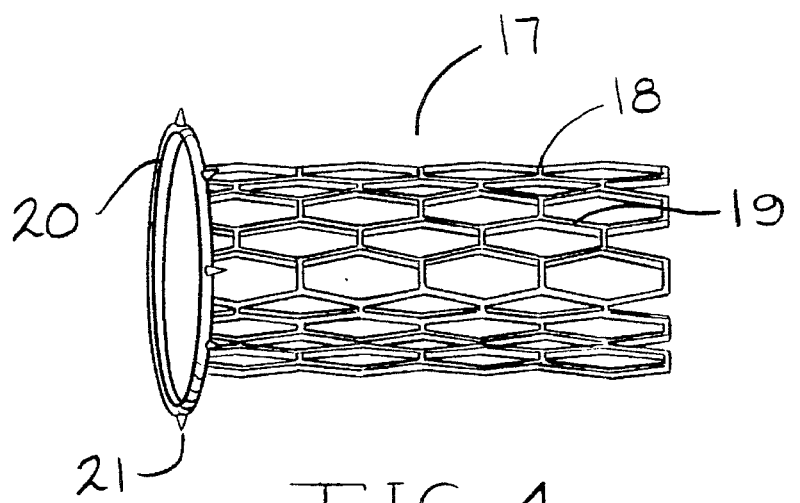
FIG. 4 is a view of the improved stent of the present invention.

FIG. 4 is a side view of the improved stent 17 of the present invention. The stent comprises a cylindrical body portion 18 made from, in the preferred embodiment, a series of stainless steel "honeycomb" sections adapted to be flexible and extremely strong for supporting and ensuring the vitality of a diseased portion of an artery. Body portion 18 is adapted to be expanded in diameter through the use of a balloon catheter interposed therein to ensure a substantially tight fit against the walls of the artery. At one end of body portion 18 is a cylindrical collar 20 having a diameter in excess of that of the body portion. Collar 20 has evenly spaced around its diameter a series of protruding tines 21 adapted to grab or catch the walls of an artery or graft as is discussed more fully below. Stent 17 may be made of a host of other materials and have various different configurations, including a solid body portion 18. The various shapes and sizes of stents are well known in the prior art.

Figure 5:
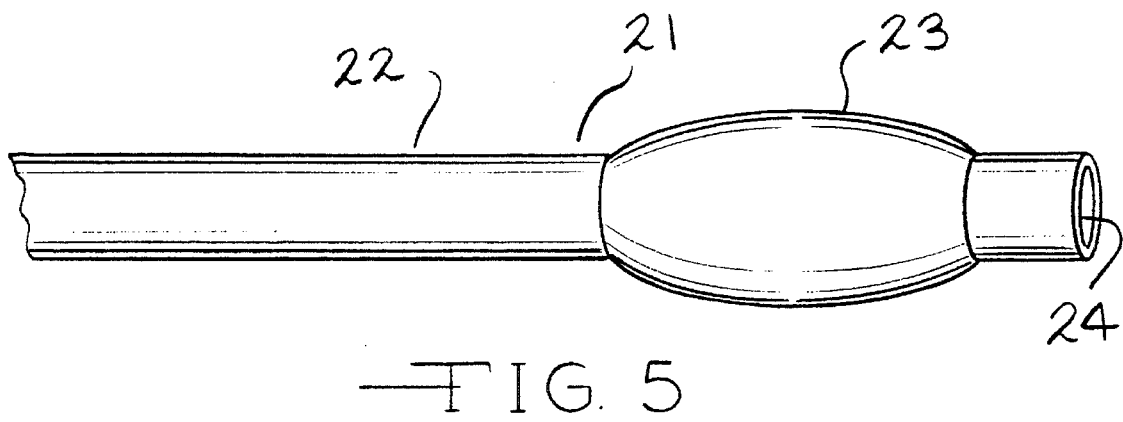
FIG. 5 is a view of a typical and well-known double lumen balloon catheter.

Adverting next to FIG. 5, a well-known double balloon catheter 21 is shown. The balloon catheter includes a hollow body portion 22 having an opening 24. The balloon catheter is adapted to be fed through the arteries and to carry visualizing instrumentation or other surgical devices within the arterial walls. A second lumen on the catheter perfuses the organ at issue (e.g., kidney). Expandable balloon 23 is interposed along body portion 22. Expandable balloon 23 may be controlled by the surgeon and may be expanded or contracted. Balloon catheter 23 is adapted to "carry" a stent into position and to be expanded for purposes of forcing a graft or stent against the walls of the artery. Deflation of the balloon allows the catheter to be removed while leaving the positioned stent or graft in place.

Figure 6:
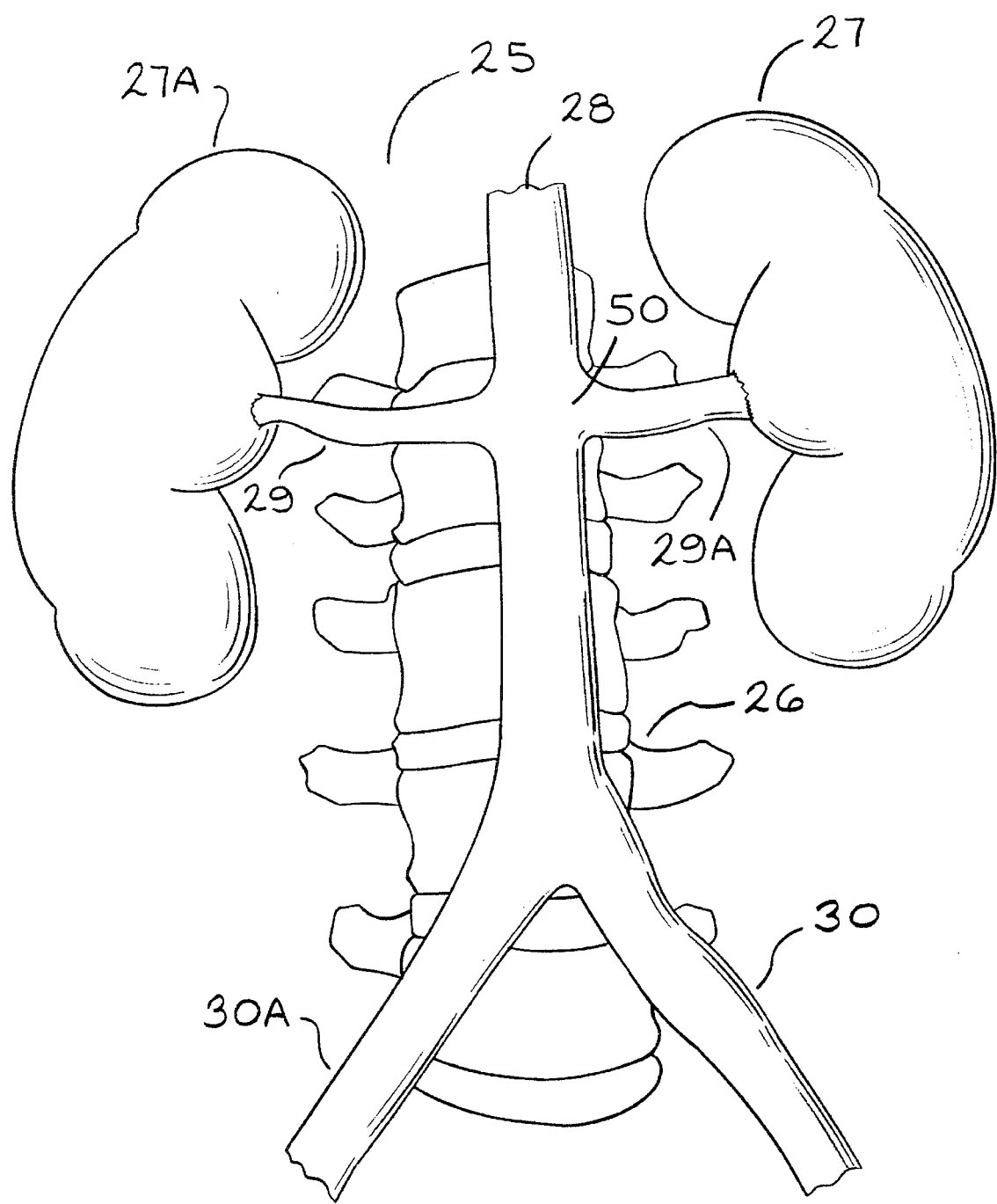
FIG. 6 is a view of the kidneys and aortic arteries interposed over the spinal column.

FIG. 6 is a view of the aorta and renal arteries, together with the kidneys. The system 25 comprises the aorta 28 extending behind the spinal column 26. Kidneys 27 and 28 are fed by branch renal arteries 29 and 29-A extending from the aorta. Ileac arteries 30 and 30-A are joined in the main portion of the aorta. The intersection between the aorta 28 and renal arteries 29 and 29-A denominated at point 50 is an area where the use of grafts or surgical techniques in the prior art to repair or remediate the aortic occlusive disease has been difficult and surgically risky. The present invention solves that problem.

Figure 7:
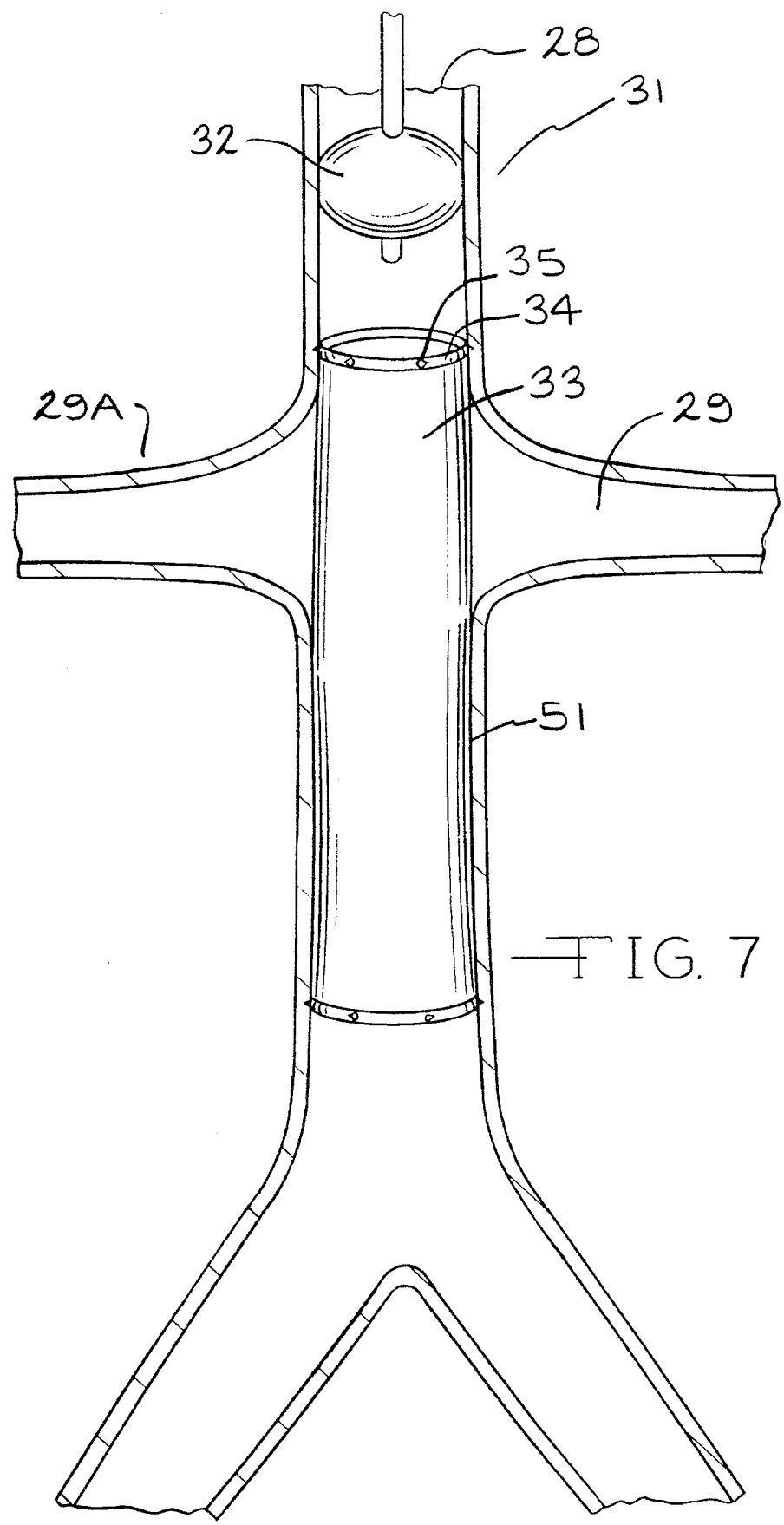
FIG. 7 is a view of the aorta and renal arteries having a graft interposed at the intersection thereof.

Adverting next to FIG. 7, the present method includes the interposition of an arterial balloon catheter 32, with balloon expanded, into the top of the aorta 28. This stems blood flow and clears the way for the remainder of the surgery and method. Graft 33 is shown to be interposed through the intersection of aorta 28 and renal arteries 29 and 29-A. Graft 33 has at each end, a collar 34 having interposed around its diameter a series of tines 35. Graft 33 is interposed in position through the use of a balloon catheter, a technique well known in the prior art. The balloon catheter is deflated and the graft is left in place. Collar 34 and appended tines 35 serve to affix the graft in place by adhering to the walls of the artery at each end of the graft. Expansion of the graft through the use of the balloon catheter also ensures that the graft body portion 33 is snugly fit against the walls of the artery at, for example, 51.

Figure 8:
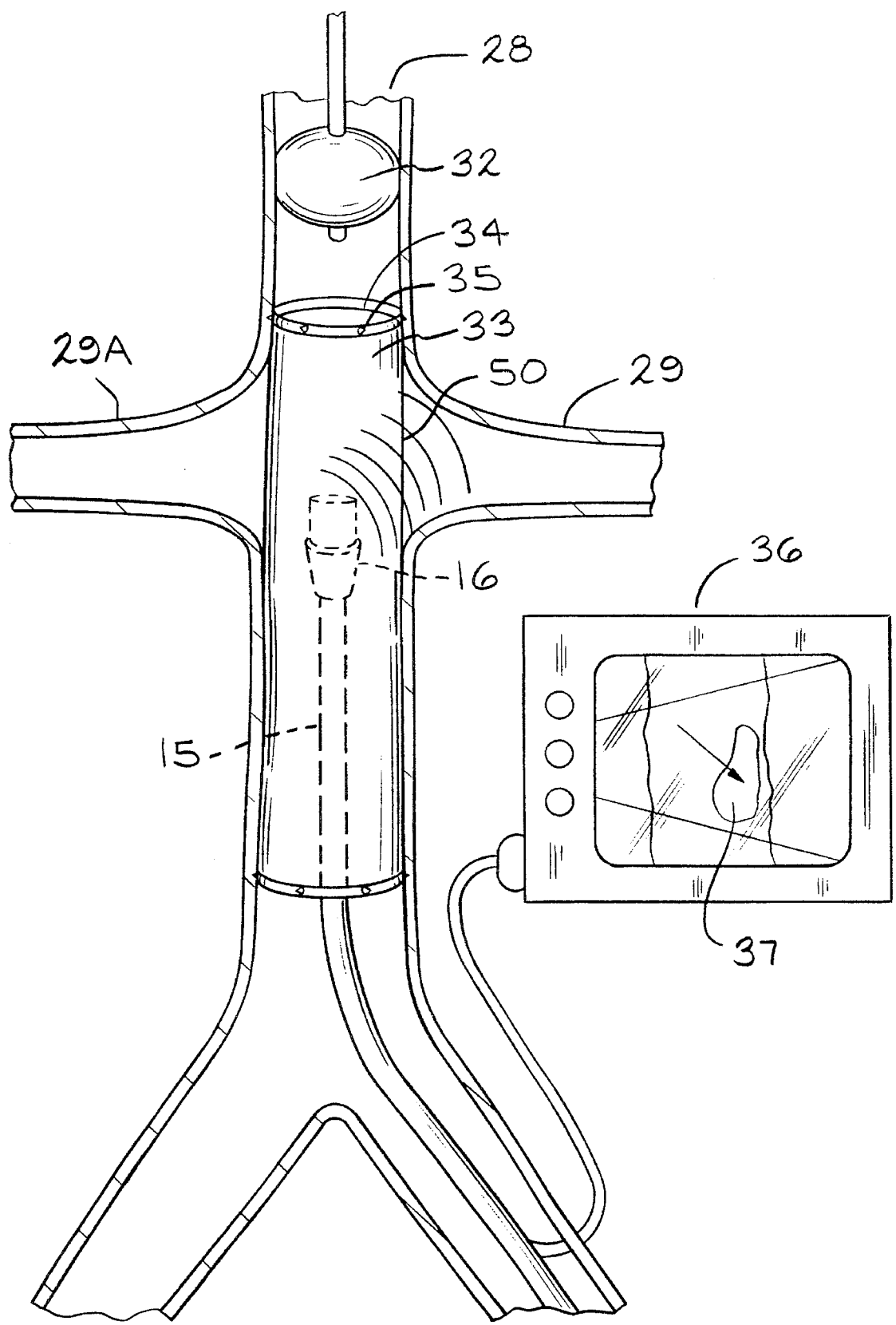
FIG. 8 is a view of the aorta and renal arteries demonstrating the use of intravenous ultrasound to detect and image the intersection point through the graft.

Adverting next to FIG. 8, once graft 33 is in place, the surgeon feeds IVUS device 15 through the ileac artery into the aorta and within the graft walls. IVUS device 15 is connected electronically to a visualizing monitor or screen 36 in the operatory and, through the use of ultrasound, is able to visualize for the surgeon the point of intersection 50 between graft 33 and renal artery 29. The intersection point is visualized on monitor screen 36 at a point 37 which the surgeon is able to measure or "mark" using well-known, accurate techniques.

Figure 9:
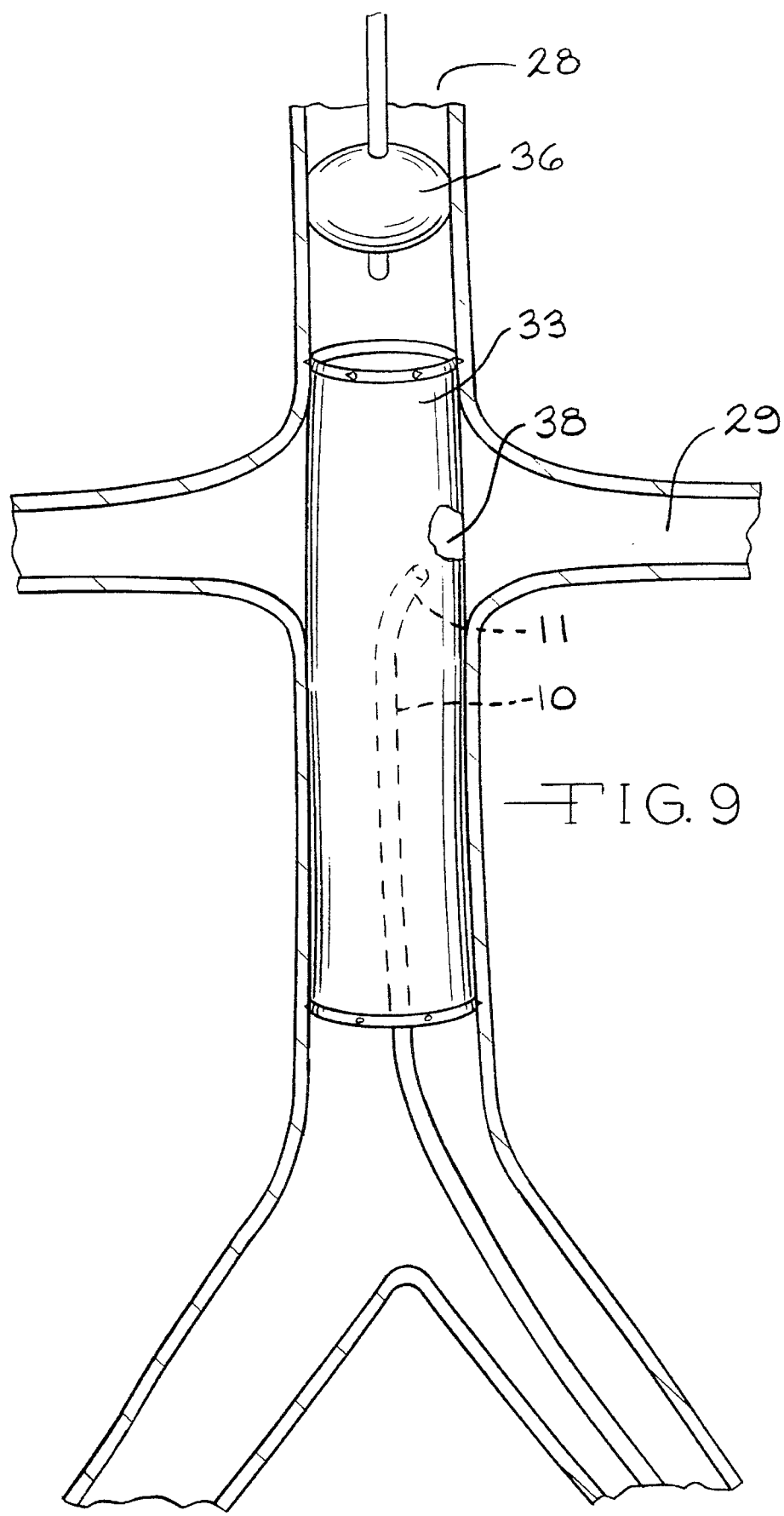
FIG. 9 is a view of the aorta and renal arteries with a laser or cautery and a created opening at the intersection of the aorta and renal arteries.

Adverting next to FIG. 9, after the point of intersection is "marked" at, for example, 37, the surgeon then inserts interarterially through the aorta and graft 33 a laser cautery device 10 having a cutting or burning device 11 at its end portion. Laser cautery device 10 is positioned by the surgeon at the visualized point of intersection between the graft 33 and renal artery 29 and an opening 38 is created through the graft at the point of intersection.

Once opening 38 is created, the surgeon is now in a position to strengthen the opening thereby allowing graft 33 to remain in place while ensuring blood flow through the renal arteries to the kidneys.

Figure 10:
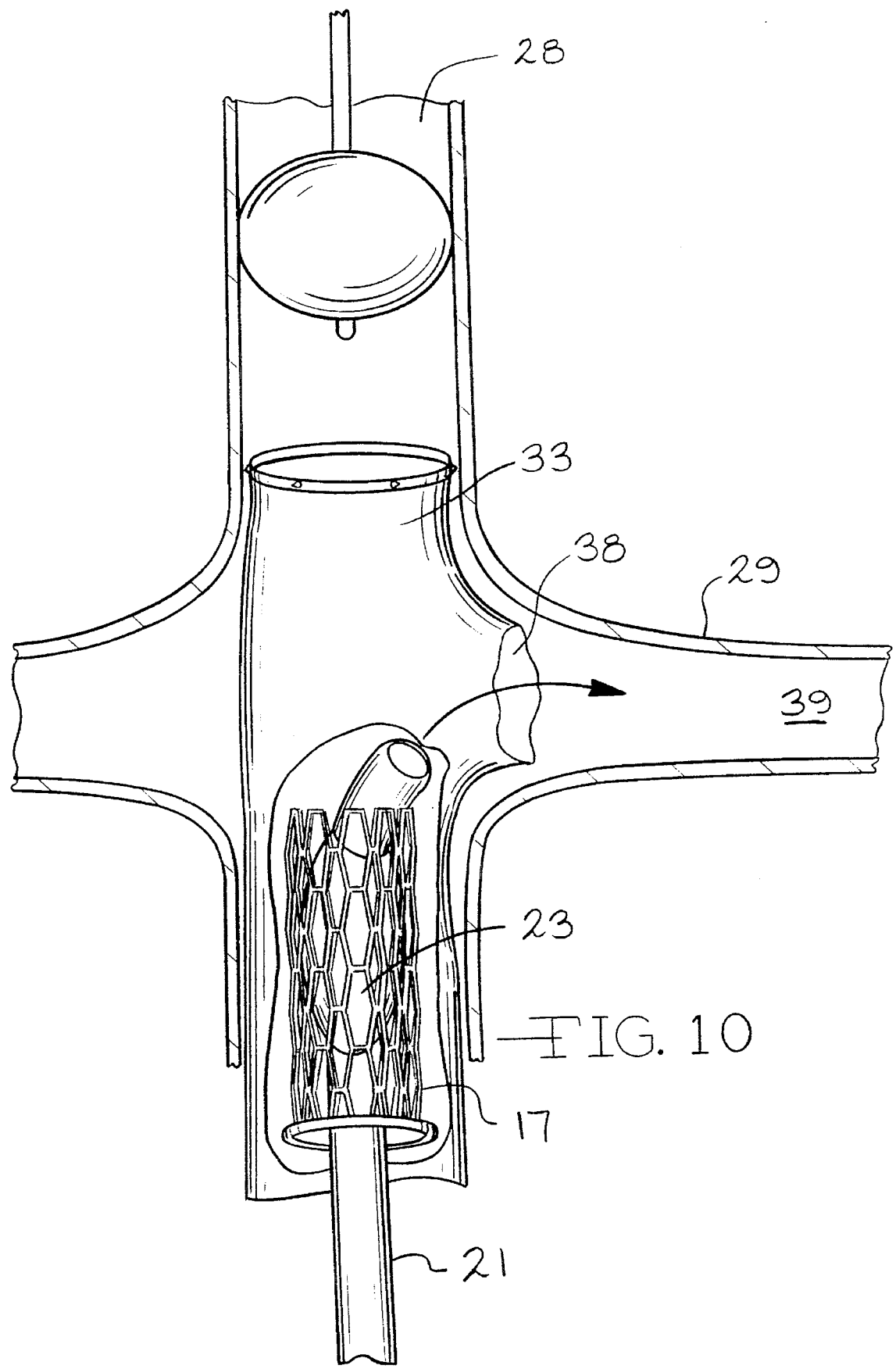
FIG. 10 is a view of the aorta and renal arteries and the use of a balloon cautery carrying the stent of the present invention toward the created opening.

Adverting next to FIG. 10, graft 33 is shown to be positioned within aorta 28 at the intersection point between the aorta and renal artery 29. Opening 38 has been created through the use of laser cautery at the point of intersection in the wall of graft 33. Balloon catheter 21 has been interposed within the body portion of stent 17 and balloon 23 has been inflated to "carry" the stent into position. The balloon catheter and appended stent are fed by the surgeon through the walls of the aorta and inserted graft 33 into a position for insertion through created opening 38. Balloon catheter 21 may also contain at its end portion an appropriate visualizing aid for locating the opening. The surgeon, through positioning the catheter and appended stent, directs the catheter and stent through opening 38 in the direction of the kidney 39 through renal artery 29.

Figure 11:
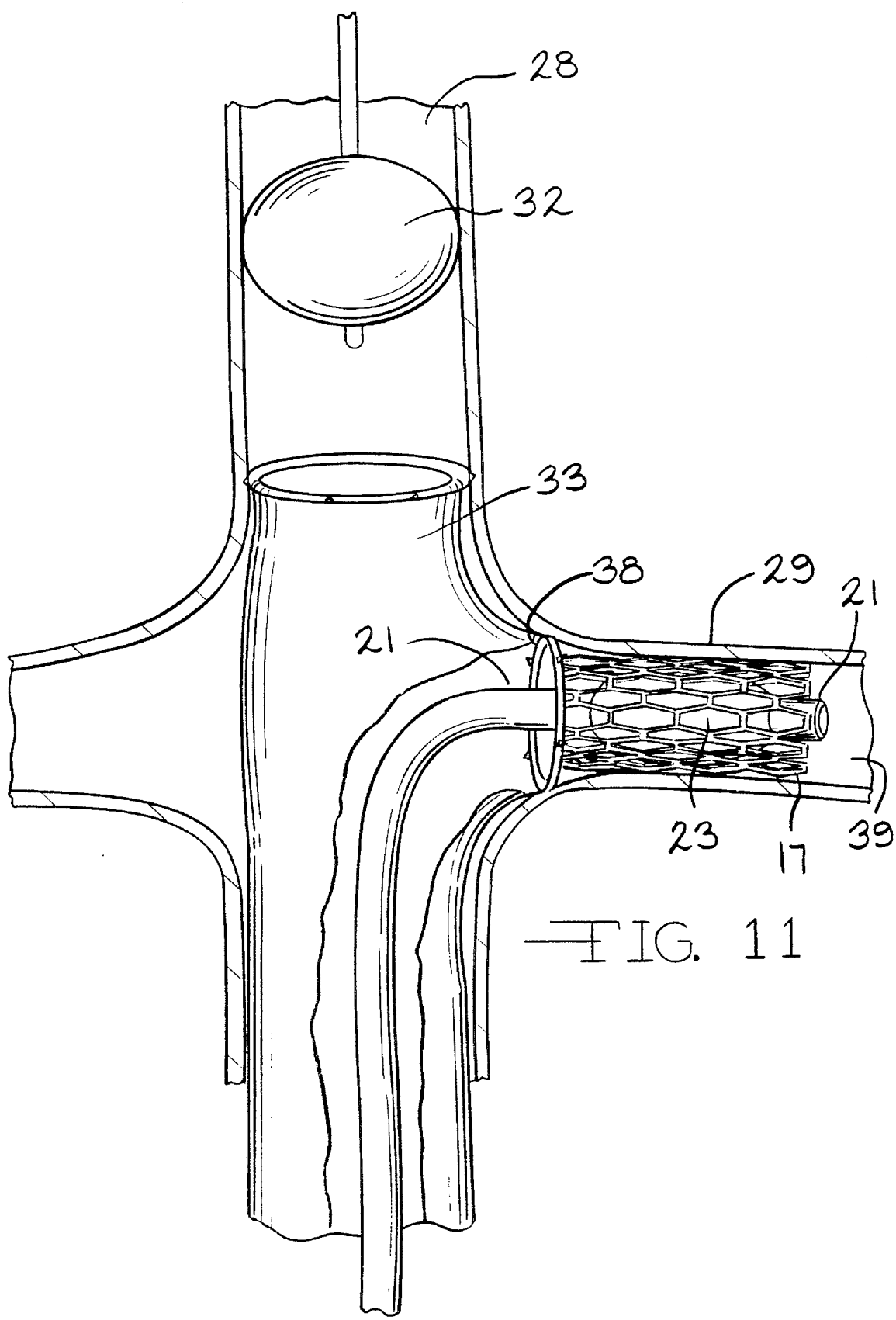
FIG. 11 is a view of the aorta and renal arteries with the stent of the improved invention interposed through the graft.

Adverting next to FIG. 11, stent 17 to be interposed down through the opening created in graft 33. Tines 21 are shown to be interposed within the graft surface to hold the stent in place. Balloon 23 of catheter 21 is then inflated to ensure firm engagement of stent 17 against the walls of artery 29. Balloon 23 can then be deflated and the balloon catheter removed from the graft and arteries.

Figure 12:
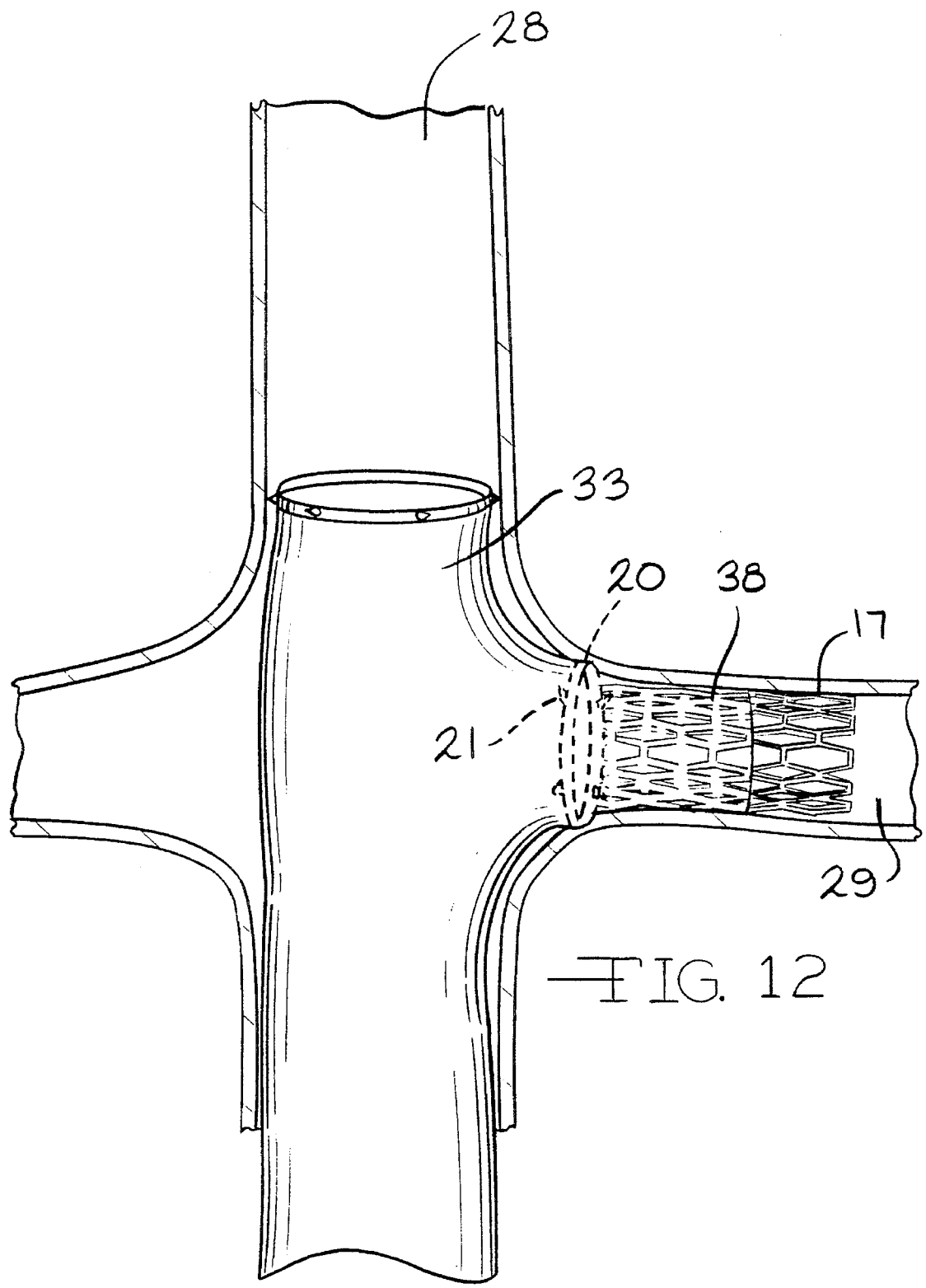
FIG. 12 is a view of the aorta and renal arteries with the improved stent of the present invention fully interposed through the graft.

Adverting next to FIG. 12, stent 17 is shown to be positioned through graft 33 and down the length of artery 29 toward the kidneys. Opening 38 has now been extended across the surface of the stent 17 and collar and appended tines 20 and 21 firmly engage opening 38 created in graft 33. Accordingly, blood flow through the aorta 28 and renal arteries 29 is ensured and, as well, any occluded area around the intersection of the aorta and renal artery is effectively repaired and strengthened.

Figure 13:
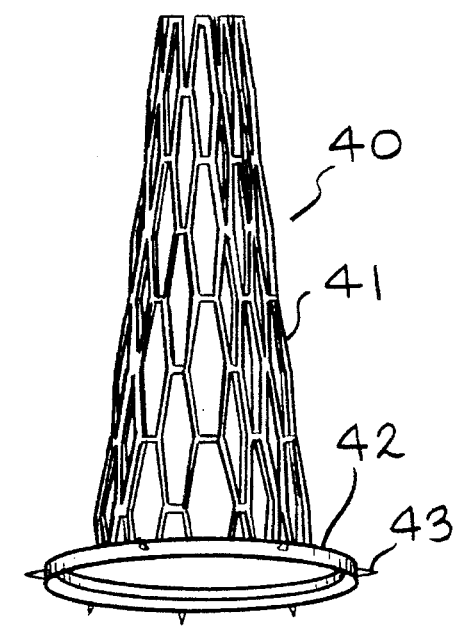
FIG. 13 is a view of another embodiment of the improved stent of the present invention.

Adverting next to FIG. 13, a second embodiment of a stent 40 is disclosed. Stent 40 includes a frusto-conical body portion 41 comprised of a mesh surface for strength. Body portion 41, as indicated, has a length of decreasing diameter and, at its larger end, has interposed around the diameter a collar 42 having a series of evenly spaced tines 43 as in prior embodiments. The frusto-conical shape of stent 40 is particularly adapted for interposition through the aorta and down the length of renal artery 29, 29-A or any other artery of decreasing diameter.

Figure 14:
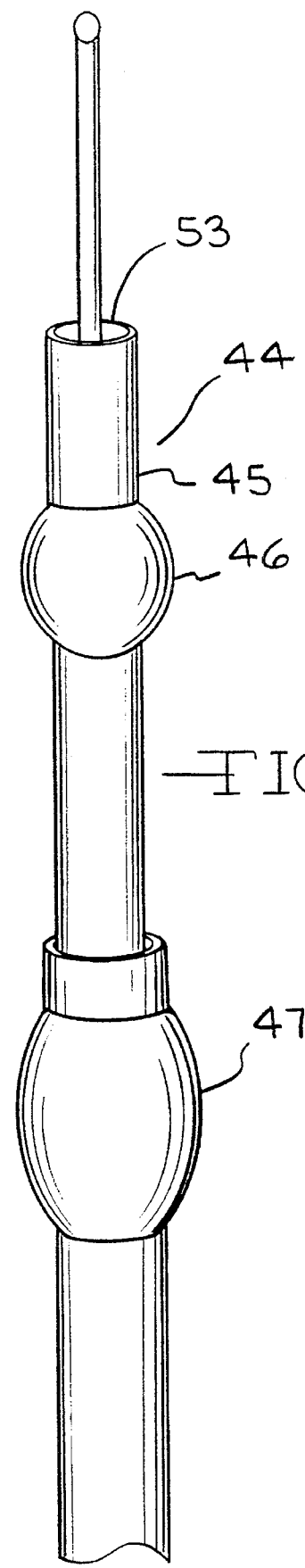
FIG. 14 is a view of a double lumen and coaxial balloon catheter typical and well known in the art.
Figure 15:
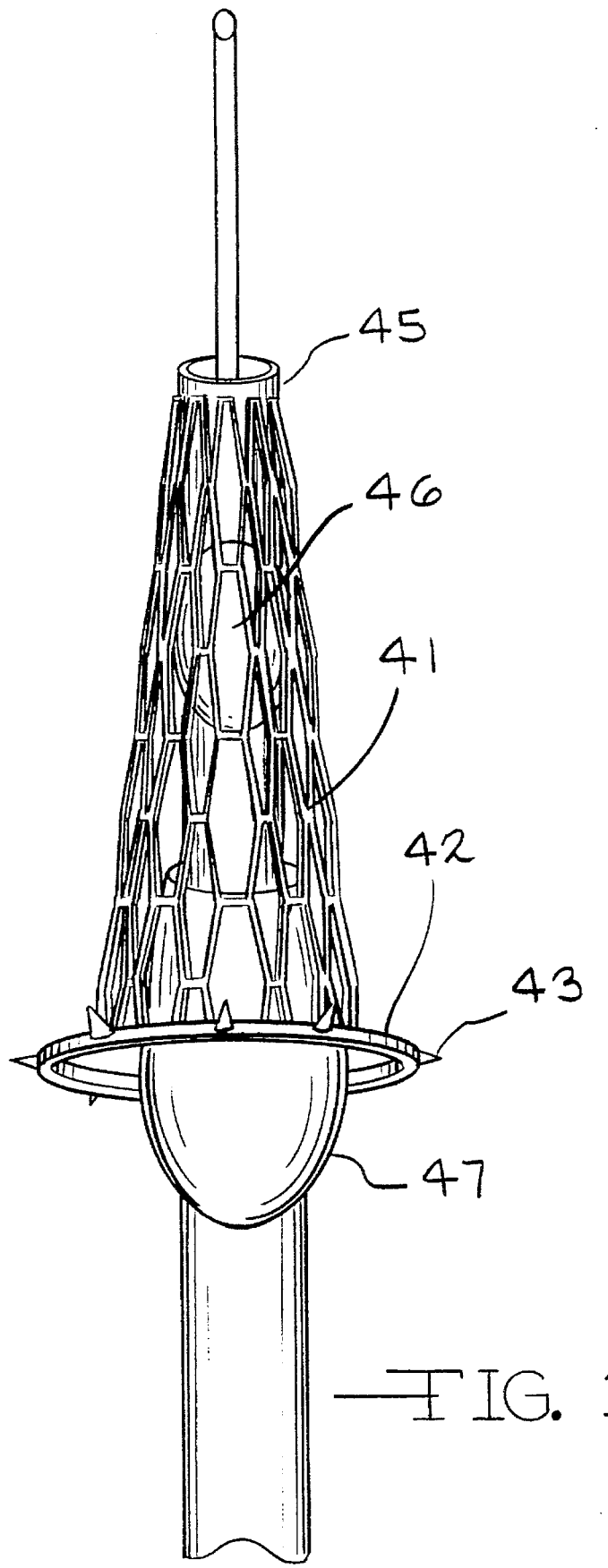
FIG. 15 is a view of a double balloon catheter carrying the improved stent of the present invention.

Further, stent 40 is adapted to be "carried" to the insertion point by a double lumen balloon catheter illustrated in FIG. 14. Double catheter 44 comprises a body portion 45 having an opening 53 through the length thereof and includes a first balloon 46 and a second balloon 47. The balloons, well known in the prior art, are inflatable and deflatable by the surgeon. Balloon 46 is generally smaller in size than balloon 47 and accordingly, as is illustrated in FIG. 15, stent 40 is interposed over double balloon catheter 44 in a manner such that the smaller balloon 46 resides in the area of stent 40 having the smallest diameter, while larger balloon 47 is positioned at the end of the stent including the collar portion and larger diameter. The double catheter is inserted in the identical manner previously described in, for example, FIG. 10, and, once in position, balloons 46 and 47 are inflated and deflated and otherwise manipulated to ensure collar portion 42 and tines 43 engage the opening. As well, stent body portion 41 is thereby snugly engaged against the walls of the decreasing diameter of the renal artery. Accordingly, the dimensional characteristics of improved stent 40 make it directly applicable to arteries of decreasing diameter such as the renal artery and further serves to ensure the best and snuggest fit possible while maintaining blood flow through the artery and attendant aorta at the point of intersection.

Accordingly, the present invention describes an improved stent and method for insertion thereof that can be readily adapted and used for the surgical treatment of aortic occlusive disease in or around the point of intersection of the aorta and other arteries through the use of a well-known graft and improved stent.

Many modifications to the invention would be apparent to one of skill in the art. For example, stent configurations and grafts of various dimensions, materials and size could easily be adapted for use with the invention. Moreover, use of the collar configuration and tines is readily adaptable to use with grafts only or stents and the surgeon may chose to use the stent alone or graft in various other parts of the arterial system whether involving intersections of arteries or not.

Positioning of the graft and stents is shown to be accomplished through the use of a balloon catheter. Other methods of positioning the stent would equally be applicable without varying from the scope and purpose of the invention. These and other modifications to the invention fall well within the scope of the following claims and will be apparent to one of skill in the art.

I claim:

1. A method for treating arterial disease at an intersection of two arteries, using a graft and stent, comprising the steps of:

providing a graft adapted to be inserted into an artery to be treated;

inserting said graft using a balloon catheter in positioning said graft to a point of intersection of two arteries to be treated;

identifying a point within said graft located at the intersection of the arteries to be treated;

manufacturing an opening in said graft at the point of said intersection of said arteries to be treated;

inserting a stent through said opening thereby creating a pathway between said arteries to be treated;

affixing said stent to said graft at the opening;

whereby the cooperation of the graft and stent inserted through the opening ensures the flow of blood at the intersection of the arteries to be treated.

2. The method according to claim 1 wherein said identifying step is accomplished using an intravenous ultrasound system.

3. The method according to claim 1 wherein the manufacturing step comprises using an electrocautery laser device.

4. The method according to claim 1 wherein said affixing step comprises the use of a plurality of tines interposed around the diameter of said stent.

5. The method according to claim 1 wherein said stent is adapted to be expanded within the walls of said artery.

6. The method according to claim 1 wherein said affixing step comprises the use of a collar having a plurality of tines interposed on the diameter of said stent.

7. The method according to claim 1 wherein said stent is frusto-conical in shape.

8. The method according to claim 1 wherein said stent is cylindrical in shape.

* * * * *